United States Patent [19]
Nieves et al.

[11] Patent Number: 5,378,430
[45] Date of Patent: Jan. 3, 1995

[54] STEAM STERILIZATION PROCESS MONITOR

[75] Inventors: Judith Nieves, Newark; Raymond P. Larsson, Denville, both of N.J.

[73] Assignee: Pymah Corporation, Flemington, N.J.

[21] Appl. No.: 133,508

[22] Filed: Oct. 7, 1993

[51] Int. Cl.[6] .............. G01N 31/22; G01K 11/06; G01K 11/12
[52] U.S. Cl. .................... 422/57; 374/160; 374/162; 374/106; 116/207; 116/219; 422/58
[58] Field of Search ............ 374/102, 106, 160, 162; 116/207, 217, 219; 422/56, 57, 58; 435/31; 436/1

[56] References Cited

U.S. PATENT DOCUMENTS

| | | | |
|---|---|---|---|
| 3,981,683 | 9/1976 | Larsson et al. | 374/106 |
| 4,382,063 | 5/1983 | Romito et al. | 422/57 |
| 4,410,493 | 10/1983 | Joslyn | 116/219 |
| 4,448,548 | 5/1984 | Foley | 422/58 |
| 5,120,137 | 6/1992 | Ou-Yang | 374/160 |
| 5,158,363 | 10/1992 | Speelman et al. | 116/219 |

FOREIGN PATENT DOCUMENTS 3210907  10/1983  Germany ................ 374/106

*Primary Examiner*—Diego F. F. Gutierrez
*Attorney, Agent, or Firm*—Anthony Lagani, Jr.

[57] ABSTRACT

An improved steam sterilization process monitor is disclosed comprising a backing strip, a wicking means in intimate contact with an organic compound mounted on the backing strip and a water vapor rate controlling cover strip. In the preferred embodiment the backing strip comprises aluminum foil having a polypropylene interlayer adhesively bonded thereto. The sole means for bonding the cover strip to the backing strip is by heat sealing. The cover layer is heat sealed to the backing strip over the entire land area of the backing strip surrounding the wicking means, but is not heat sealed to the wicking means. The organic compound has a normal melting point in the absence of water vapor of about 5° to about 50° F. above a predetermined control temperature.

17 Claims, 1 Drawing Sheet

FIG. I
PRIOR ART
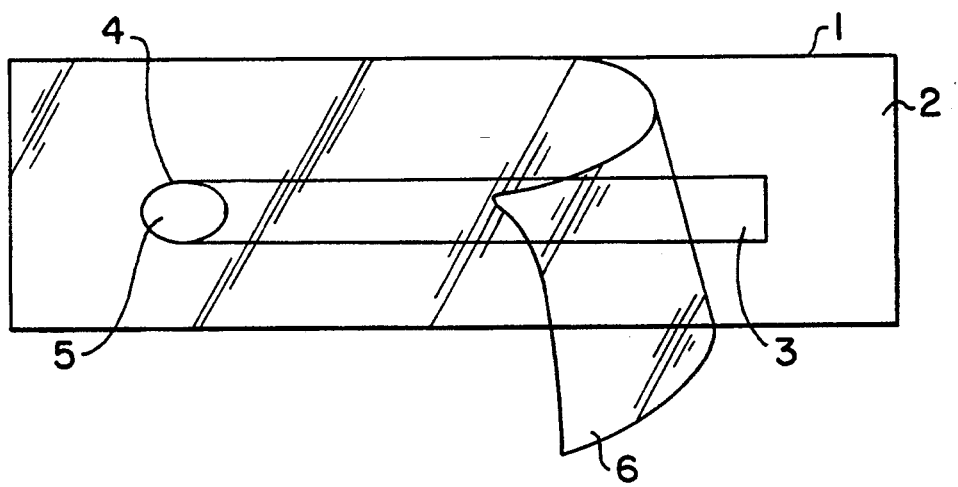
FIG. 2
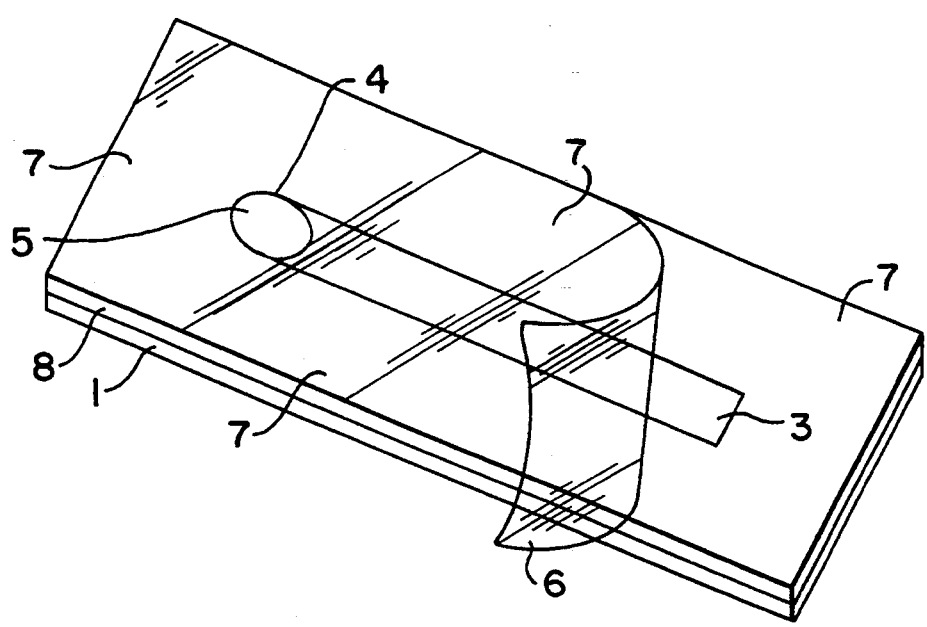

STEAM STERILIZATION PROCESS MONITOR

FIELD OF THE INVENTION

This invention relates to a steam sterilization process monitor. In particular it relates to a steam sterilization process monitor of the integrating type.

BACKGROUND OF THE INVENTION

It is well known that heat will destroy microorganisms. The presence of moisture accelerates this destruction by denaturing or coagulation of the protein making up the microorganism. The importance of moist heat in the sterilization process has been known for about 100 years. While Pasteur had established the fact that temperatures above the boiling point of water were required to kill many organisms, it was not until 1880 that a steam pressure sterilizer was developed. However, there was no significant notice of the need for sterilization of hospital equipment and fabrics until the introduction of first antiseptic and then aseptic surgery.

About the turn of the century manually controlled sterilizing autoclaves were introduce into hospitals. Their efficiency left much to be desired, but nonetheless, this was a definite step forward. As a result of advances in the food industry a fuller understanding of parameters required for spore kill were developed, and it was determined that the order of death was logarithmic.

The most significant aspect in the development of safe and effect sterilization techniques was the recognition of the presence of moisture in the killing of microorganisms. Most microorganisms contain sufficient moisture so that moderate heat alone, e.g., 80°-100° C., will destroy the microorganism. Most bacterial spores, however, contain substantially no moisture. Their destruction by dry heat alone requires elevated temperatures in excess of 150° C. Such excessive temperatures can result in the destruction of the article to be sterilized, or otherwise seriously limit its useful life. Hence, in the hospital arena pathogenic spores are destroyed using a steam atmosphere In autoclaves.

While the first effective steam sterilizers were conventionally operated at about 250° F. for sterilization cycles of about 12 to 15 minutes, the preferred sterilization conditions, presently, are about 270° F. for about 3 minutes.

Lacking any adequate means of monitoring the process, to ensure an adequate safety margin, sterilization times as long as thirty minutes have been used to ensure that 100% of the pathogenic spores have been killed. Such long sterilization cycle times give the operator a degree of confidence that steam has penetrated throughout the autoclave and among all of its contents. However, long heating cycles are disadvantageous from the stand point of economy of time, energy consumption and deleterious effects of the materials to be sterilized, e.g., fabric gowns, drapes, muslin products, certain plastic devices, etc. For these and other reasons there was a continual attempt to develop methods to confidently monitor the sterilization process so that time exposure could be minimized.

Initial attempts at monitoring the steam sterilization process relied on chemical type indicators. The crudest variety comprise a sealed tube containing a compound with a melting point which corresponds to the sterilization temperature to be achieved. One of the earliest of such devices was sold under the name DIACK ™. See for example U.S. Pat. Nos. 3,313,266; 3,341,238 and 3,652,249. These devices are capable of doing no more than indicating whether or not the autoclave has reached the melting point of the chemical in the lube for a time sufficient to melt the chemical.

Other sterilization process monitors rely on a temperature accelerated reaction to cause color change in an indicator. Though some of these devices purport to be operative at more than one temperature/time condition, they suffer from the disadvantage that they do not match the spore kill temperature/time relationship.

The thermal resistance of spores of a particular species at any temperature is characterized by its temperature coefficient. The symbol $Q_{10}$ is used to designate the temperature coefficient over a range of 10° C., and is the ratio of the death rate constant at a particular temperature to the death rate constant at a temperature 10° C. lower. Generally, the measurements are made for a fixed time interval, e.g., 9 minutes. If the constants at two temperatures, $t_1$ and a temperature, $t_2$, 10° C. higher are known, $Q_{10}$ may be calculated from the equation $$\log Q_{10} = \frac{10}{t_2 - t_1} \log \frac{K_2}{K_1}$$

wherein $t_1$ and $t_2$ are as defined and $K_1$ and $K_2$ are the respective death rate constants.

Where temperature is expressed In degrees Fahrenheit the relationship is described in terms of Z number rather than $Q_{10}$. The relationship is described by the following formula:

$$t = F_o \times 10^{(250-T)/Z}$$

wherein $t$ is the kill time for spores at T° F and $F_o$ is the kill time for spores at 250° F.

Spores generally exhibit a $Q_{10}$ value of about 10[°C.], or a Z number of 18[°F.]. Therefore, it is desirable to have a sterility indicator which will, in a sense, mimic spore kill. To do so, the ratio of the effect of temperature as a function of time on a measurement taken at one temperature as compared to the same measurement at another temperature 10° C. lower should also be 10. To be useful as a sterility indicator, this relationship must also be dependent on the presence of moisture, since the spore kill time/temperature relationship is vastly different in the dry or wet state. In the absence of moisture spore kill at 270° F. is negligible, but in the presence of steam spore kill is virtually complete for the most resistant strains at these temperatures in about 1-2 minutes.

From time to time attempts have been made to develop sterilization indicators which permit quality control of sterilization with the confidence that all microorganisms have been destroyed. In the past, the most satisfactory method has been the use of spore strips. Spores which are particularly difficult to destroy are selected as the control standard, e.g., Bacillus Subtilis vat., Niger and Bacillus Stearothermophilus. The spore strip is placed in the autoclave with the materials to be sterilized. At the end of the sterilization cycle, the spore strip is studied to determine whether it is possible to grow organisms in a suitable culture medium. Failure of the spores to reproduce indicates death of spores; and hence, adequate sterilization.

Although this control technique is accurate, it suffers from several inherent disadvantages, (1) excessive cost (2) delay between processing and control data (3) batch to batch variation of the spores and (4) heat resistance of spores decreases with storage time.

The first successful chemical type steam sterilization process monitor to mimic spore kill was that of the Larsson U.S. Pat. No. 3,981,683, incorporated herein by reference. This device comprised a backing strip, a chemical compound whose normal melting point was above the sterilization temperature to be monitored, the chemical compound being mounted on the backing strip toward one end thereof, a wicking means in contact with and extending away from the chemical compound toward the distal end of the backing strip, and a cover strip which is rate controlling with respect to the ingress of steam. The chemical compound is selected so that its melting point is depressed by the absorption of water passing through the cover strip in the vapor phase. Although Larsson disclosed that the cover strip could be adhered to the backing by adhesive bonding or heat sealing, no guidance is given with respect heat sealing techniques.

An attempt was made to develop a heat sealed device of the Larsson '683 type device. See U.S. Pat. No. 4,410,493, which issued covering a heat sealed device. Attempts to commercialize the device failed. The patent discloses that the cover layer should be adhered to the backing strip and wicking means by heat sealing thereby enclosing the entire device by full contact of the cover layer with the backing, chemical compound and wicking means.

An improved device of the Larsson type was patented to Foley with the issuance of his U.S. Pat. No. 4,448,548, incorporated herein by reference. The improvements disclosed by Foley were the ability to control the speed of advance of the color front produced by the wicking of the chemical compound. This control is attributed to the selection of an acrylic adhesive and the incorporation into the chemical compound of a binder such as polyvinyl pyrrolidone.

Both Larsson and Foley commercialized their devices by utilizing an adhesive to secure the cover strip to the backing. Until recently these devices have operated successfully in all types of sterilizers including high vacuum units. In conventional sterilization processes the item to be sterilized is wrapped in a fabric wrapping with the sterilization monitor enclosed therein. A unique application for the device has been the monitoring of the sterilization process in the operating room where "flash sterilizers" were used to sterilize materials required immediately during an operation in progress. In this sterilization process the items to be sterilized as well as the sterilization process monitor are laid exposed and unwrapped in the flash sterilizer. No problems had been encountered in using the sterilization monitors in this application until the recent advent of high vacuum flash sterilizers.

The fact that the sterilization monitor lies exposed in the flash sterilizer exposes it directly to the high vacuum and steam. The method of operating the flash sterilizer is to expose the materials to be sterilized to alternating cycles of steam at about 134° C. and high vacuum. The first cycle is a steam cycle followed by a high vacuum cycle. The result is that the monitors of Larsson which are adhesively sealed, are directly exposed to the hot steam resulting in softening of the adhesive. The subsequent high vacuum cycle causes the adhesive, weakened by high temperature exposure, to give way resulting in failure of the device.

What is required is an improved sterilization monitor of the type described which will withstand the adverse conditions of a high vacuum flash sterilizer.

SUMMARY OF THE INVENTION

It has surprisingly been found that an improved steam sterilization process monitor of the type disclosed by Larsson U.S. Pat. No. 3,981,683, and Foley U.S. Pat. No. 4,448,548 can be made to withstand the adverse conditions of high vacuum and high temperature of a flash sterilizer by heat sealing the cover strip to the backing while avoiding sealing the cover strip to the wicking means. This is accomplished by heat sealing only in the land area surrounding the wick and chemical compound.

BRIEF DESCRIPTION OF THE DRAWINGS

FIG. 1 is a partially exploded view of a prior art sterilization process monitor.

FIG. 2 is a partially exploded view of the sterilization process monitor of this invention.

DETAILED DESCRIPTION OF THE INVENTION

This invention relates to an improved integrating type steam sterilization process monitor capable of direct exposure to high temperature and high vacuum without failure of the device by rupture of the integrity of the seal between the rate controlling cover strip of the device and the backing strip. It will be appreciated by those skilled in the art that the sterilization process is intended to result in 100% spore kill of any pathogenic spores. The disclosures of Larsson '683 and Foley '548 will be set forth herein in sufficient detail in order to illustrate the advantages of the instant invention.

FIG. 1 shows a typical structure for the sterility indicator of the Larsson '683 invention. A backing strip, 1, is coated with a thin layer of adhesive, 2, a wicking means, 3, is positioned on the backing strip with one end in communication with a depression or pocket, 4, embossed into the backing strip, 1. A pellet of organic compound, 5, is inserted into the pocket, 4, and in communication with the wicking means, 3. A cover strip, 6, is then pressed in place on top of the device, the cover strip, 6, being adhesively bonded in place.

The composition of the backing strip is not critical. It, however, must be dimensionally stable at the process temperature being monitored. Although polymeric materials can be used, in order that they have substantial dimensional stability, they must be of a heavier gauge than desired from the standpoint of economics and overall thickness of the device. Additionally, the embossing of the pocket requires the application of heat and pressure. Hence, the preferred backing strip is metal foil, e.g., aluminum foil. Though the thickness of the foil is not critical, it is preferred that foil of about 1 to 5 mils is used e.g. 3 mils. Any of the polymers used as the cover strip can be used as the material of construction of the backing strip. However, the backing strip in that event is preferable at least about 10 mils in thickness more preferably about 20 to 30 mils. The term "dimensionally stable" as used in the specifications and claims with reference to the backing strip means that the backing strip will not change dimensions by shrinkage, wrinkling etc. as a result of exposure to process temperatures.

The wicking means may be any suitable material through which the organic compound can migrate by capillary action. The preferred wicking means is a paper strip. Other such wicking means such as non-woven polymeric fabrics and inorganic fibrous compositions may be used.

The dimensions of the wicking means is not critical. However, its dimensions (thickness and width) will affect the rate of wicking and determine the quantity of organic compound required to result in a suitable scale length. Hence, from an economic standpoint the wicking means should be as thin as practical. A suitable width for the wicking means is about 3/16 to about ⅜ of an inch, e.g. ¼ of an inch in width.

Illustrative, non-limiting examples of the wicking means which may be used are Whatman Nos. 1, 5 and 5410 filter papers, Whatman No. 114 filter paper, Schleicher & Scheull No. 410 & 598 paper, supported microcrystalline cellulose (TLC plate), supported aluminum oxide, and supported silica gel.

The cover strip is a rate controlling film which permits moisture (gaseous) to pass through at a rate sufficient to depress the melting point of the organic compound to the sterilization temperature to be monitored. The necessary vapor transmission rate will of course depend on the operating temperature and the organic compound selected.

It is possible to make a precise determinations of vapor transmission rate as a function of temperature for various films and the effect of water vapor on melting point depression of various compounds. These data may then be used to select combinations of cover strip vapor barrier and organic compound suitable for a particular temperature to be monitored. Such a fundamental approach to component selection is neither necessary nor desirable, since it is only approximate, and an actual trial must be made in any event. Hence, an Edisonjan approach results in the most rapid method of selection.

In selecting the rate controlling cover strip, it is of course necessary that the polymeric composition of the cover strip is not subject to attack by the organic compound. For example, mylar (polyethyleneglycol terephthalic acid ester) may not be used where the organic compound is a hydroxy containing aromatic compound, e.g., alkyl substituted phenols. Illustrative examples of suitable cover strip material are mylar, polypropylene, polystyrene and polymethylmethacrylate. Of course it will be obvious to those skilled in the art having access to this disclosure, that the polymers may not be used at or above their softening point. The cover strip should be transparent and preferable clear. A preferred cover strip material is polypropylene since it has a high softening point and is relatively inert to most chemical compounds. Additionally, it has an acceptable water vapor transmission rate at temperatures about 250° F. to 270° F., the temperature at which hospital sterilization processes are usually carried out.

The thickness of the cover strip film will of course effect the vapor transmission rate. Preferably the cast film has a thickness of about 0.75 to about 3 mils, more preferably about 1 to about 2 mils, e.g., 1.25 mils.

The term "rate controlling" when used in the specification and claim with respect to the cover strip means that the cover strip controls the water vapor transmission rate by virtue of its permeability to water vapor at the temperature to be monitored. No effort is made to determine the actual vapor transmission rate or in any other way to control the vapor transmission rate.

In selecting a system for a sterility indicator, the first step is to select a cover strip and backing strip. As a first choice aluminum foil is selected as the backing strip and polypropylene is selected as the cover strip. The wicking means is, typically, conventional filter paper, e.g., S&S 410 filter paper. It then is only necessary to select a suitable organic compound.

In selecting the organic compound for the purposes of this invention, it must be a compound in which water has at least a slight degree of solubility. The compound selected should have a normal melting point about 5° to about 50° F. greater than the sterilization temperature to be monitored; more preferably, about 8° to about 40° F.; most preferably, about 10° to about 30° F. greater than the temperature to be monitored, e.g., 20° F. greater.

That water be soluble in the organic compound to a slight extent is essential to the operation of the device of this invention. Not wishing to be bound by theory, it is believed that the water acts as a melting point depressant. The object in selecting an organic compound having a melting point higher than the temperature to be monitored, but capable of having its melting point depressed by the absorption of water is to insure that the device will be inoperative in the absence of water vapor at the control temperature. The term "control temperature" as used in the specification and claims means the temperature to be monitored for the process in question, e.g., sterilization, pasteurization, etc.

Though it is possible to determine the actual degree of water solubility in the organic compound, it is not essential. In addition to having the specified melting point as described above, the compound should contain functional groups which will result in a degree of water solubility. Illustrative of the functional groups which the organic compound must contain are aidehyde, carbonyl, ester, keto, ether, hydroxy, amino, amide, carboxy, phosphate, phosphonate sulfones, sulfate, sulfonate, etc. Structurally, illustrative non-limiting examples of these functional groups are:

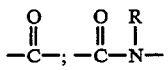

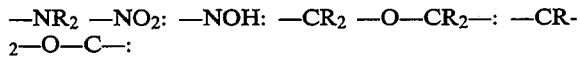

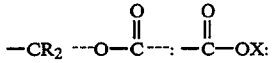

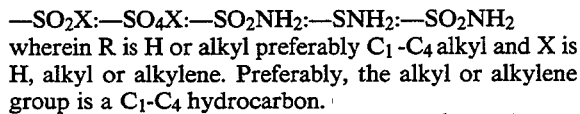

—SO₂X:—SO₄X:—SO₂NH₂:—SNH₂:—SO₂NH₂ wherein R is H or alkyl preferably $C_1$-$C_4$ alkyl and X is H, alkyl or alkylene. Preferably, the alkyl or alkylene group is a $C_1$-$C_4$ hydrocarbon.

Hence, the organic compounds of this invention are heterogeneous compounds which must contain oxygen or nitrogen in the structure. In addition to oxygen and nitrogen, other non-reactive substituents may be included such as chlorine, sulfur, phosphorus, etc.

The term "organic compound" as used in the specification and claims means an organic compound containing in its structure at least one oxygen or nitrogen atom as well as carbon atoms. As stated above, other atoms can be included in the structure. Illustrative examples of organic compounds suitable for use in the practice of this invention are 2-chloracetamide, ethoxy benzamide, benzoic acid, diphenyl succinate, dichlorophenol, dimethyl phenol, benzamide, urea, 1,4 dihydroxybenzophenone, hydroquinone, dioxime, ethyl ester of toluene sulfonic acid, phenacetin, salicylamide and salicylic acid.

In the Larsson and Foley devices of the prior art it is preferred that the cover strip be adhered to the backing strip with an adhesive. Heat sealing, however, can be used instead of adhesives. Any adhesive for bonding polymers to metal or polymers to polymers can be used. The adhesive of course must be resistant to attack by the organic compound. The preferred adhesives are silicone adhesives, e.g., General Electric Company's Sil Grip 574 and acrylic adhesives.

In the practice of this invention heat sealing is used as the sole means of bonding the cover strip to the backing. In preparing sterility indicator for a given application, as a first approximation, aluminum foil is used as the backing strip, and polypropylene film is used as the rate controlling cover strip. An organic compound having a normal melting point about 20°-30° F. above the control point is selected. A pocket or depression is embossed into the backing strip and a pellet of the organic compound is placed in the pocket. The wicking means is aligned to the backing strip with a portion of one end over the pellet. For convenience of preparation the backing strip is first coated with a thin line of adhesive material in the proposed location of the pellet and wicking means. Thus the pellet and wicking means will remain in place. In order to be able to heat seal the cover strip to the backing a film of polypropylene is adhesively adhered to the backing strip. The cover strip is then pressed in place and heat sealed to the polypropylene layer of the backing strip.

The system is tested by placing it into a steam autoclave held at the control temperature and at the corresponding saturated steam pressure. After about twelve minutes the device is removed from the autoclave and observed. No additional wicking should occur after removal from the autoclave. Not wishing to be bound by theory, it is believed additional wicking after removal from the autoclave or at temperatures below the control temperature are the result of supercooling or the formation of a supersaturated solution of water and organic compound which permits wicking below the control temperature.

If no wicking occurs after dropping the temperature and the length of wicking of organic compound along the wicking means is satisfactory to give an acceptable scale for the desired application, the screening test is continued.

Additional tests should be conducted about 5° F. above and below the control temperature to determine the $Q_{10}$ value for the compound selected. Where it is desired to have a $Q_{10}$ which matches a particular process, e.g., spore kill, it may be necessary to repeat the tests utilizing other organic compounds and/or polymers for the cover strip.

It has been found that the $Q_{10}$ value is effected by the nature of the cover strip. For example whereas a sterility indicator which uses polypropylene as the rate controlling cover strip and ethoxy benzamide as the organic compound as a $Q_{10}$ of about 18[°F.]. When mylar (polyethyleneglycol terephthalic acid ester) is used as the cover strip the $Q_{10}$ is about 4–5[°F.].

Since most organic compounds are colorless, it is desirable to include a dye in the organic compound to make it visible on the wicking means. Alternately, the dye may be applied to the initial portion (nearest the pellet of organic compound) of the wicking means. As the organic compound moves along the wick it picks up dye stuff and carries it along the wicking means. Any suitable dye which is soluble in the organic compound may be used. Illustrative examples of such dyes are: ethylene blue, crystal violet, malachite green, brilliant green, methyl violet and methyl green.

Where the organic compound is acid or basic it may be made visible by presaturating the wicking means with a suitable pH sensitive dye. As the organic compound wicks along the wicking means it will cause a color response change in the pH sensitive dye. Illustrative examples of such pH sensitive dyes are phenolphthalein, xylenol blue, Nile blue A, m-cresol purple, bromocresol green, thymol blue, bromophenol blue, alizarin, bromphenol red, methyl red, brilliant yellow, phenol red, etc.

The contribution of Foley '548 to the sterilization monitoring art was an improvement in the Larsson device which permitted the manufacture of a shorter less expensive device. This was accomplished by the discovery that the use of an acrylic adhesive would cause the migration rate of the organic chemical compound to slow down. Similarly, by utilizing a pelletized chemical which incorporated therein a binder, e.g., polyvinylpyrrolidone, the operation of the device was further slowed down resulting in a shorter wicking distance. In order to eliminate failures resulting from the particular chemical compound selected and commercialized by Larsson, Foley utilized salicylamide, one of the organic compounds disclosed by Larsson. The result of these three changes resulted in a shorter running device requiring less material, and hence, resulting in significant cost reductions. The reduced size of the Foley device permits it to tolerate the high vacuum cycle of the vacuum flash sterilizer more readily than the larger device sold under the trademark Thermalog ® by PyMaH Corporation.

The instant invention resolves the adhesive bonding failure problems of the prior art devices by utilizing heat sealing in a particular manner.

Referring now to FIG. 2, in one embodiment of the invention, the heat sealing is limited to the land area, 7, surrounding the wicking means, 3, and the pellet of organic compound, 5. An essential aspect of the invention is that either the upper surface or lower surface of the wicking means must be free of bonding to a surface. In the preferred embodiment the wicking means is tacked to the backing strip, 1, with a small amount of adhesive (not shown). Heat sealing only in the land area, 7, leaves the upper surface of the wicking means unbonded to the cover strip. Not wishing to be bound by theory it is believed that it is essential that air in the device be free to flow back over the wicking means. In the case of the Joslyn U.S. Pat. No. 4,410,493 device, unsuccessful commercialization of its heat sealed device was a result of the fact that the wicking means was adhesively tacked to the backing strip, and additionally heat sealed to the cover strip, 6. The result was that as the organic compound wicked along the wicking means it pushed air contained in the wicking means ahead of it. Because the device was completely sealed the air had nowhere to go. As air pressure built up, the flow of material along the wick stopped. By leaving at least one surface of the wicking means free of bonding to the cover strip or backing strip, air is able to flow backward along the wick in the space between the wicking means and the cover strip thereby relieving pressure build up, and permitting free movement of the organic compound along the wicking means.

It will be appreciated by those skilled in the art that an alternate structure is to position the wicking means on the cover strip by adhesive tacking. The adhesive tacking is necessary only to ensure that the wicking means is properly positioned in the device with respect to the organic compound.

In an alternate solution to the wicking means positioning problem, the wicking means can be brought into contact with the pellet of organic compound, heated to cause sufficient melting of chemical to adhere the wicking means to the pellet, and then placing the pellet in the embossed pocket, 4. The result is that the wicking means is properly positioned without adhesive tacking to either the backing strip, 1, or the cover strip, 6. The result is a free flow area for air both above and below the wicking means.

In order to heat seal to the foil backing strip it is necessary to use a backing strip to which the cover strip can be heat sealed. Where the backing strip utilizes aluminum foil it is necessary to coat the surface with a substance to which the polymeric cover strip will bond. The preferred backing strip, is a polymer/aluminum foil laminate backing strip. The preferred polymer is polypropylene. Referring again to FIG. 2, the backing strip, 1, has laminated to it a one mil film of polymer, 8. The cover strip, 6, is heat sealed to this polymer interlayer, 8. While polypropylene has been successfully utilized as the interlayer, 8, it will be appreciated by those skilled in the art having access to this disclosure that any material to which the cover strip, 6, can be heat sealed is suitable for the interlayer, 8. Illustrative non-limiting examples of suitable interlayer materials are polypropylene and Surlyn®, a polyethylene ionomer. The interlayer can be adhesively bonded to the aluminum foil backing strip. In one embodiment the polymeric interlayer can be laminated to the aluminum foil using an acrylic adhesive.

The polymer interlayer composition should be selected to be compatible with the cover strip composition from the stand point of heat sealing characteristics, and should not soften to the extent that its bond to the backing strip will be deleteriously affected. Additionally, the interlayer must be non-reactive with the organic compound, and sufficiently heat deformable to permit embossing of the backing strip to accept an organic compound pellet. Such selection is well within the skill of those skilled in the at of heat sealing. Generally, most polymeric thermoplastics will meet these latter specifications. However, polyethyleneglycol terphthalate ester films of more than several mils in thickness may prove difficult to emboss.

In heat sealing the cover strip, 6, to the interlayer coated backing strip a heated platen is placed below the device and a pressure platen having a relieved recess in the shape of the wick and pellet is brought down in contact with the cover strip and pressed against the heated platen. The result is that a seal is formed around the wick and pellet over the entire land area, 7. The heat sealing temperature will depend upon the material utilized for the cover strip. Where the polymeric interlayer and the cover strip are both polypropylene the heat sealing temperature is preferably about 290° F. to about 310° F. The pressure contact time is about 2 seconds to about 5 seconds. The term "land area" as used in the specification and claims means that area of the backing strip which is not occupied by the wicking means and the pellet of chemical compound.

In carrying out the heat sealing process it is necessary that the heating platen used for sealing be relieved in the area of the pellet as well as the wick. In that way the wicking means is not sealed to the cover strip on at least one surface. This permits an unrestricted flow of air along the wick backward toward the pellet, thereby eliminating the resistance to wicking caused by back pressure.

EXAMPLE 1

A 3 mil sheet of aluminum foil was coated with an acrylic adhesive, Isotac ™ 460 manufactured by 3M corporation and a one mil film of polypropylene (Exxon Extrel ™ 50) adhered thereto. Bonding was accomplished by passing the composite through nip rolls without deforming the aluminum. This composite was used as the backing strip, 1, of the integrating sterilization monitor. A pocket, 4, was embossed into the backing strip, 1, and a 75 mg. pellet of phenacetin was inserted into the pocket.

A wick was cut out of a sheet of Schleicher & Scheull S&S 598 paper having dimensions of ¼ inch in with and 3½ inches long. The wick was placed in position on the backing strip, 1, and tacked into place using acrylic adhesive. The cover strip, 6, of one mil polypropylene was placed over the device and heat sealed over the land area only, using the above described heat sealing platen. In the practice of this invention it is preferred to chill the pellet down to about 40°-50° F. before heat sealing to ensure that the pellet does not met during the heat sealing step.

The sterilization monitor was tested in a high vacuum autoclave by placing it exposed in a tray in the autoclave. The device was subjected to a heating cycle of 3 minutes at 270° F., and the subjected to a vacuum of 28 inches of mercury. The test was repeated for a different device at 250° F. and the $Q_{10}$ of the device calculated. The device had a $Q_{10}$ of 7.9, which substantially mimics spore kill. Devices made using Whatman #1 paper and S&S 410 paper had $Q_{10}$ values of about 7. While these devices do not have the most preferred $Q_{10}$ of 10, the are adequate for monitoring steam sterilization processes.

What is claimed is:

1. A sterility indicator device for use in a steam autoclave to determine the degree of completion of a steam sterilization process at or about a predetermined control temperature, the process being intended to result in 100% spore kill of any pathogenic spores, the control temperature being about 250° F. to about 270° F., comprising:
   (a) a backing strip consisting essentially of an aluminum foil having adhesively laminated thereto a polymeric film, said backing strip having a pocket or depression embossed therein;
   (b) an organic compound having a normal melting point which is about 5° to about 50° F. above the predetermined control temperature, said normal melting point being depressed below said control temperature by the absorption of water into the organic compound when said organic compound is exposed to saturated steam at about the control temperature, said normal melting point of the organic compound being above the control temperature, said organic compound containing at least one functional group selected from the group consisting of ether, amide and hydroxy, the organic compound being mounted on the backing strip in the pocket or depression at a first end of said backing strip;

(c) a wicking means having a first end of said wicking means in intimate contact with said compound, said wicking means extending away from compound to a second distal end of said backing strip; said organic compound and wicking means defining a land area comprising the portion of the backing strip not covered by the organic compound and wicking means; and (d) a water vapor transmission rate controlling cover strip covering said compound and wicking means, said cover strip being permeable to water vapor and having a water permeability coefficient at the control temperature such that sufficient water vapor will permeate the cover strip to reduce the melting point of the organic compound from its normal melting point to at least the control temperature, the cover strip comprising polypropylene film of about 0.75 to about 3 mils in thickness;

said device being unresponsive to heat at the control temperature in the absence of steam, and displaying a visual response of the integrated time/temperature exposure of an article to be sterilized to moist heat; the cover strip covering the backing strip, wicking means and organic compound, and being bonded only to the land area of the backing strip by heat sealing.

2. The device according to claim 1 wherein the polymeric film is polypropylene.

3. The device according to claim 1 wherein the cover strip comprises polypropylene film.

4. The device according to claim 1, with the visual response showing a wicking distance of the organic compound indicative of 100% spore kill.

5. The device according to claim 1 wherein the organic compound has a normal melting point of at least 40° F. above the control temperature.

6. The device according to claim 1 wherein the organic compound has a normal melting point of at least 20° F. above the control temperature.

7. The device according to claim 1 wherein the cover strip is about 1 to 2 mils in thickness.

8. The device according to claim 1 wherein the organic compound contains at least one functional group selected from the group consisting of ether and amide.

9. The device according to claim 1 wherein the organic compound contains at least, one functional group selected from the group consisting of amide and hydroxy.

10. The device according to claim 1 wherein the organic compound is salicylamide, ethoxy benzamide or phenacetin.

11. The device according to claim 1 wherein the organic compound contains an ether group and an amide group 12. The device according to claim 1 wherein the organic compound is salicylamide.

13. The device according to claim 1 wherein the organic compound is phenacetin.

14. The device according to claim 1 wherein the organic compound has a normal melting point of about 5 to about 50 degrees above the control temperature.

15. The device according to claim 14 wherein the organic compound has a normal melting point of at least 5° F. above the control temperature.

16. The device according to claim 1 wherein a dye is included in the organic compound.

17. The device according to claim 1 wherein the polymeric film is adhesively laminated to the aluminum foil utilizing an acrylic adhesive.

* * * * *